United States Patent [19]

Sheriff

[11] Patent Number: 4,931,775
[45] Date of Patent: Jun. 5, 1990

[54] PLANT WATERING NEED MONITOR

[76] Inventor: Jack W. Sheriff, 2167 Calle Guaymas, La Jolla, Calif. 92037

[21] Appl. No.: 222,640

[22] Filed: Jul. 21, 1988

Related U.S. Application Data

[63] Continuation-in-part of Ser. No. 53,706, May 26, 1987.

[51] Int. Cl.$^5$ ............................................. G08B 21/00
[52] U.S. Cl. ...................................... 340/604; 340/693;
73/336.5; 324/696; 200/61.05
[58] Field of Search ................. 340/604, 693; 343/825;
324/65 P, 61 P; 73/335, 336, 336.1, 338.6, 338,
304 R; 200/61.05

[56] References Cited

U.S. PATENT DOCUMENTS

| | | | |
|---|---|---|---|
| 3,927,370 | 12/1975 | De Bough | 340/693 |
| 3,961,247 | 6/1976 | Toki | 324/65 R |
| 3,968,428 | 7/1976 | Numoto | 324/65 P |
| 4,020,417 | 4/1977 | Brehob et al. | 324/65 R |
| 4,137,931 | 2/1978 | Hasenbeck | 324/65 P |
| 4,268,824 | 5/1981 | Phillips | 340/604 |
| 4,350,040 | 9/1982 | Fasching et al. | 73/304 C |
| 4,503,707 | 3/1985 | Rosa et al. | 73/336.5 |
| 4,514,722 | 4/1985 | Batcheler et al. | 340/604 |
| 4,621,229 | 11/1986 | Hirth | 324/65 R |

OTHER PUBLICATIONS

"Water Warbler", Electronics Australia vol. 37 No. 9 pp. 42–43; D. Edwards.

Primary Examiner—Josesph A. Orsino
Assistant Examiner—Jill Jackson
Attorney, Agent, or Firm—Henry J. A. Charmasson

[57] ABSTRACT

An alarm device for monitoring the watering needs of a plant which comprises a stick surmounted by a cylindrical box containing the electrical elements. The stick is buried in the soil of a pot holding a plant. The alarm device is powered by a battery easily installable and consists of a conductive probe detector located at the buried end of the stick. It also comprises a first integrated circuit which is switched by a backwards connected amplifier acting as a very high impedance switch which minimizes power consumption. The circuit emits a series of pulses when a threshold resistance level is reached. These pulses trigger a melody integrated circuit which produces a pleasant singing melody destined to draw the attention of the plant grower to the watering needs of a plant. The tune is repeatedly reproduced until the soil resistance detected by the probe detector has exceeded a threshold resistance level.

14 Claims, 2 Drawing Sheets

PLANT WATERING NEED MONITOR

PRIOR APPLICATION

This is a continuation-in-part of application Ser. No.: 07/053,706 filed 5/26/87 which is now abandoned.

FIELD OF THE INVENTION

This invention relates to soil moisture detectors, more specifically to an alarm device for monitoring the watering needs of a plant.

BACKGROUND OF THE INVENTION

Moisture sensors are increasingly found in regulating devices, in particular in air moisteners. They have also been used in soil moisture regulation, more specifically in greenhouses where the air and the soil must be simultaneously maintained at fixed levels of moisture. Generally, the moisture sensors found in industrial greenhouses are sophisticated and expensive devices monitored by computers or full time operators in connection with watering devices or humidifiers. These devices are activated when the moisture level falls below a predetermined level by means of appropriate alarms and/or software. Other types of industrial monitoring unrelated to plant watering needs are also sophisticated devices, such as U.S. Pat. No. 4,350,040.

Some prior art also exists for monitoring the watering needs of house plants. These devices measure soil impedance changes across probes placed proximate to the plant. As soil moisture changes, the impedance changes until a set point is reached and an indicator signals the need for watering, as shown in U.S. Pat. No. 4,020,417. Some of these monitors are related to or have been developed from the sophisticated devices used in industrial applications. These sophisticated devices may provide a means to precisely and linearly calibrate the device (such as taught by U.S. Pat. No. 4,621,229) and/or include precise temperature compensators (such as disclosed in U.S. Pat. No. 3,961,247). Also as a carry-over from the industrial grade equipment, an audible alarm is also used an an indicator of watering needs.

In contrast to the precision, availability of power, operators and automatic devices in an industrial application, house plant monitoring devices are typically battery powered, precision and temperature compensation is unnecessary and full time operators are not present. Battery life is a key consideration in the in-home application. Although, the majority of the time, the current drain on the battery is expected to be caused by the monitoring of the soil probes, the current draw of the watering need indicating means must also be limited to prolong battery life since the house may be empty for extended periods.

The need for extended battery life in these in-home applications has lead to sophisticated sampling and monitoring circuits to minimize the monitoring drain on the battery, such as taught in U.S. Pat. No. 4,514,722. LED indicators, piezoelectric ceramic beepers, and DC to DC converters are also employed to minimize current draw (U.S. Pat. No. 4,514,722). These approaches have increased battery life, but have resulted in a sophisticated device.

What is needed is a small, low cost, in-home monitor of soil moisture, not an adaptation of industrial grade equipment. The power requirements and irritating audible alarms of industrial grade equipment also may not be appropriate for the home environment.

None of the prior art the applicant is aware of incorporates a monitoring circuit that draws less than 5 microamps or provides a pleasant indicator of watering needs. The prior art current drain results in the need for sophisticated sampling circuits or space consuming larger batteries in order to obtain a battery life in excess of one year.

SUMMARY OF THE INVENTION

The principal and secondary objects of the invention are:
 to provide a simple long lasting in-home alarm device for monitoring the watering needs of a plant;
 to provide a compact stick like device to be buried in the soil; and
 to provide an alarm device which draws attention of the plant grower by producing a pleasant melody whenever the moisture of the soil containing plant has fallen below a predetermined threshold. These and other objects are achieved by an alarm device in the form of a stick surmounted by a cylindrical box containing the electrical elements. The stick is buried in the soil of a pot containing a plant. The alarm device is powered by a battery easily installable and consists of a conductive probe detector, located at the tip of the stick to be covered by the soil. It also comprises a first integrated monitoring circuit which is fed by an amplifier connected as a very high impedance switch, which drastically minimizes current drain on the battery. The integrated circuit emits a series of pulses when a threshold resistance level is reached and the amplifier allows significant current to be drawn. These pulses trigger a melody designed to pleasantly draw the attention of the plant grower to the watering needs of a plant. The tune is repeatedly reproduced until the soil resistance detected by the probe detector has exceeded a threshold resistance level.

DESCRIPTION OF THE PREFERRED EMBODIMENT

Figure 1:
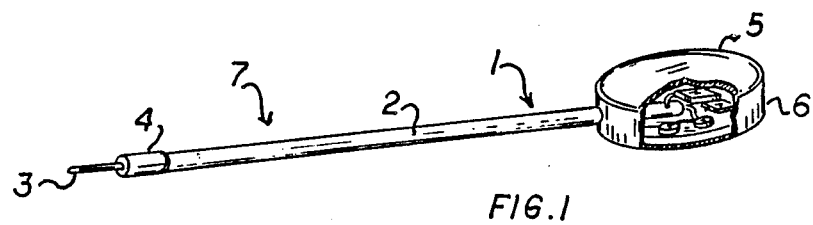
FIG. 1 illustrates one preferred embodiment of the present invention.

FIG. 1 shows the preferred embodiment of the present invention. The alarm device 1 consists of a stick 2, typically of length between 5.0 and 15.0 centimeters, terminated in a wire 3. The stick 2 typically takes the form of a metallic barrel surrounding the wire 3 on almost all its length. The stick 2 and the wire 3 insulated inside the stick 2 are electrical conductors, preferably made of stainless steel. They constitute the two electrodes of a conductive moisture sensor or probe 7. A plastic cap 4 insulates the two electrodes at the extremity of the stick 2.

The stick 2 is surmounted by a cylindrical box 6 which contains the electrical elements. The box 4, preferably made of plastic, includes a lid 5 which can be removed for the installation of a new battery. In operation, the stick 2 is planted into the soil contained in the plant pot on all its length. The cylindrical box 5 rises above the surface of the soil and can be inconspicuously hidden in the foilage of the plant.

Figure 2:
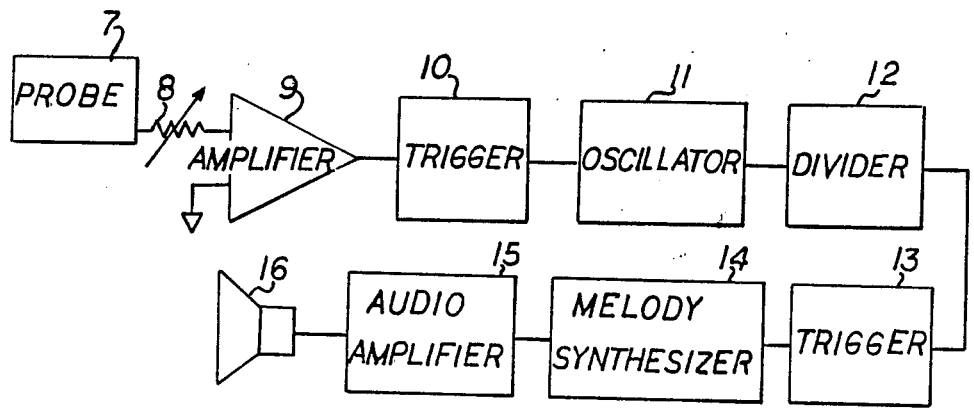
FIG. 2 shows a block diagram schematic of a circuit made in accordance with the preferred embodiment illustrated in FIG. 1.

Referring now to FIG. 2, there is illustrated a block diagram schematic of a circuit made in accordance with the preferred embodiment of the present invention. The probe 7 serves as the invention's input signal. The probe 7 consists of a humidity sensor. Several humidity sensors are already known. In the preferred embodiment, a resistance sensor (2,3) is used. It typically consists of the metallic barrel 2 and of the wire 3, as shown in FIG. 1. The length and spacing of the electrodes determine the resistance threshold necessary to trigger a resistance level. It should, however, be understood that any other moisture sensor such as a capacitance moisture sensor, would be suitable for the present invention. The conductivity of the soil between the two electrodes varies with the degree of moisture as well as with other factors such as the mineral content of the soil. When the water is consumed or evaporates, the soil dries out, causing the conductivity of the material between the electrodes to decrease. Since the amount of watering varies with each plant, the preferred embodiment of the invention is provided with the variable resistor control 8. This variable resistor control 8 is accessible to the user and can be calibrated in accordance with the amount of water required for a particular plant. The input signal measured between the electrode of the probe 7 and controlled by the variable resistor 8 is subsequently amplified by a level amplifier 9. The level amplifier 9 is connected and constructed so that the input and output signal constantly remain in phase.

If the output level of the level amplifier 9 falls below a threshold value, the trigger 10 is activated causing the oscillator 11 to oscillate. A divider 12 reduces the frequency of the oscillator pulses. The rising edge of a positive pulse originating from the divider 12 activates another trigger 13, allowing a melody chip 14 to cycle once through a predetermined tune. After one pulse has activated a trigger 13 and thereby the melody chip 14, the tune is repeatedly reproduced until the probe signal changes and exceeds the threshold level. Such change normally occurs when the plant is being watered again.

In order for the melody chip signal to be audible in normal conditions, a low power audio amplifier 15 amplifies the audio signal originating from the memory chip 14 and transmits it to a speaker 16.

Figure 3:
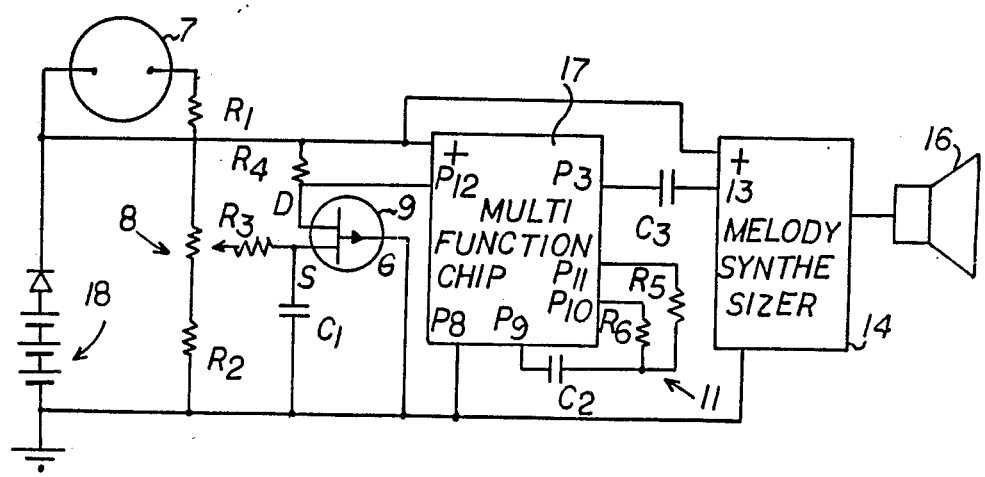
FIG. 3 shows exemplary circuitry for the preferred embodiment illustrated in FIG. 1.

Referring now to FIG. 3, there is shown exemplary circuitry of all the elements shown in FIG. 2. The current flowing through the electrodes of the probe 7 is passed across a resistance R1 and directed to the variable resistor 8. The resistance value of R1 is typically 100 Kilohms. The variable resistor is grounded via a resistor R2, typically of value of 1 megaohm. The variable resistor 8 can vary between 0 ohm and 1 megohm.

The current then flows into a level amplifier 9 across a resistor R3, of 1 megohm in the preferred embodiment of the present invention. The level amplifier 9 is typically an FET switch. Preferably, the level amplifier is realized in the following configuration. The gate terminal G is grounded, the drain terminal D is connected to the voltage source through a load resistor R4 whereas source terminal S is connected to the signal input resistor R3 and to a filtering capacitor C1 of capacitance 0.1 microfarad. The capacitor C1 is also grounded. Such a configuration provides a great stability in the circuit and create a very high input impedance. The backward wiring of the FET switch results in a very low current draw. In the preferred embodiment of the present invention, the level amplifier 9 is preferably a 2N5485.

The trigger 10 of FIG. 2 consists of the Reset function port or pin 12 of an integrated circuit 17. The resistance threshold detected by the variable resistor 8 and the level amplifier 9 activates the port P12 of the integrated circuit 17, thereby activating the oscillator 11. If the resistance is less than the threshold resistance level, the current flows back into the circuit through a resistor R4, typically of 10 megohms. The intensity of the current is typically of 2 microamperes. The entire system is then in a dormant stage. If the resistance level is greater than the threshold resistance level, the oscillator 11 starts to oscillate. It consists of two resistors R5 and R6, typically of respective values 120 kilohms and 1.5 megaohms, as well as of a capacitor C2. The resistors R5, R6 and the capacitor C2, typically of capacitance 0.1 microfarad, are respectively connected to the ports P9, P10 and P11 of the integrated circuit 17. The frequency of the oscillator 11 is determined by the values R5, R6 and C2. The input impedance of the reset pin P12 is lowered once the trigger 10 has been activated. In this manner, a subsequent lower level signal does not affect the unit activation process and maintains the operation in progress. The hysteresis circuit is built within the trigger 10 so as to prevent false or multiple signals from interfering with a previous triggering threshold signal level.

A divider built within the integrated circuit 17 reduces by binary division the frequency of the oscillator pulses. Preferably, the frequency of the pulses amounts to approximately 5–6 minutes over a wide spectrum of temperatures. The integrated circuit 17 is typically a 4060 IC chip.

The positive pulse generated by the integrated circuit 17 and the divider 12 every 5–6 minutes flows from the port P3 of the integrated circuit 17 into a triggering port 13 of the melody chip 14, typically on integrated circuit, via a capacitor C3, typically of value 1 microfarad. When the trigger 13 is activated by the rising edge of a positive pulse, the melody portion of the same integrated circuit 14 is caused to cycle once through the predetermined tune. The melody integrated circuit 14 consists of etched semi-conductors which repeatedly produce the same tune once the pulse originating from the divider 12 has activated the trigger 13. The tune selected in the preferred embodiment of the present invention was the following tune: "Love Me Tender". It should be understood that any other appropriated tune would be suitable.

The integrated circuit 14 is preferably a melody IC chip, such as UM 3166-11 H. The integrated circuit 14 is further connected to a speaker 16, as previously described, via an audio amplifier not represented in FIG. 3. the device is electrically supplied by a battery 18. In the preferred embodiment, no more than three 1.5 volt, 100 microampere-hour calculator type battery cells are used for the battery power 18. If reduced battery life (or less frequent watering signals) is assumed, two 1.5 volt, 100 microampere-hour calculator battery mercury or silver oxide type cells are acceptable in the preferred embodiment. In the preferred embodiment, the unit is self testing as soon as the battery is installed, since infinite or air gap resistance will trigger melody.

An alternate configuration to allow shipment with the battery installed would include a non-conductive disposable plastic insulator placed at the battery contact points preventing power from activating the electrical circuits. Removal of plastic tab insert provides a simple method of activating and testing (in air) the unit without the need for added switches or circuitry.

Figure 4:
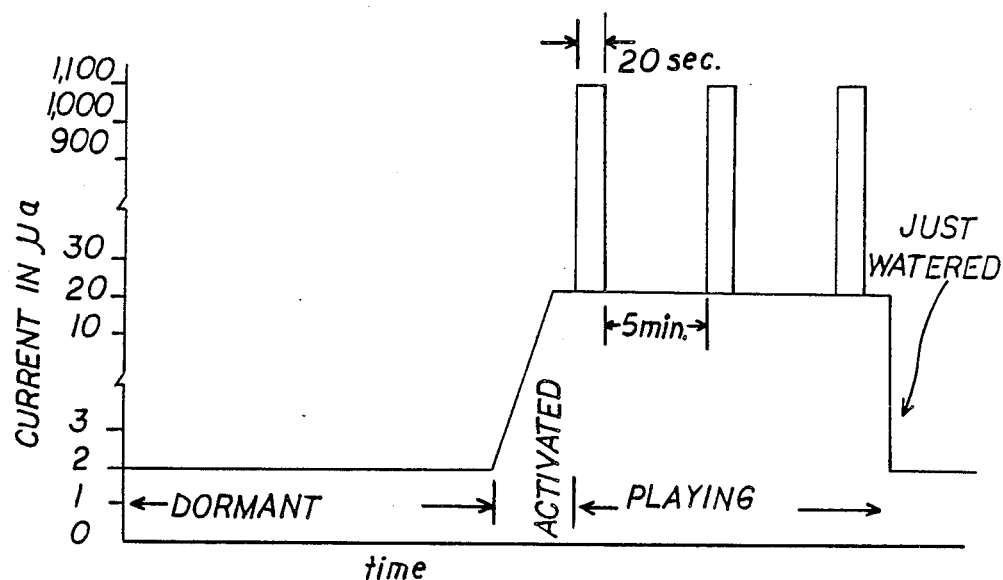
FIG. 4 shows a typical current drain during a watering cycle.

FIG. 4 shows the values of the various electrical current draws the preferred embodiment units have been set so as to meet the following technical specifications. When the probe 7 (see FIG. 1) is directly shorted (regardless of the position of the sensitivity control setting variable resistor 8 shown in FIG. 2) or threshold resistance is not present, the current flowing in the alarm circuit is typically less than 2 microamperes (dormant condition). When the unit has been activated and before the melody is being played, the current is typically less than 30 microamperes (activated). While the melody is playing, the current rate is typically less than 1000 microamperes. Watering returns the unit to the dormant state.

Considering that the melody is playing for an average of two hours after the unit has been activated and that the alarm unit of the preferred invention is normally triggered twice a week, it is expected that the battery lifetime is generally eighteen months.

The probe resistance levels are determined by the various resistors and capacitors of the alarm circuit of the preferred embodiment in order to meet the following requirements. The threshold resistance level above which the unit is activated is typically set to 200 to 300 kilohms when the center arm of the variable resistor 8 is adjacent to the resistor R2. When the center arm of variable resistor 8 is adjacent to the resistor R1, the threshold level is typically 2 to 3 megohms.

Although the previous values have been found to be particularly suited for the objective hereabove mentioned, it should be noted that other values can be selected.

While the preferred embodiment of the invention has been shown and described, changes and modifications may be made therein within the scope of the appended claims without departing from the spirit and scope of this invention.

What is claimed is:

1. An electrical device operating at low currents for signaling the watering needs of a plant by monitoring the moisture level of the soil around said plant comprising:

means for sensing said moisture level by generating an electrical signal generally proportional to said moisture level;

means for supporting said sensing means, shaped and dimensioned to be planted in said soil;

means for calibrating said device in accordance with the amount of water ordinarily needed by said plant;

a first semi-conductor switch having a drain terminal, a gate terminal and a source terminal, said drain terminal being connected to a voltage source through a load resistor, said gate terminal being connected to a signal reference ground, and said source terminal being connected to said electrical signal through a high value series resistor;

oscillating means for sending electrical pulses at a first frequency, said oscillating means being connected to said drain terminal and being triggered when the voltage differential between said signal and said voltage source causes a certain current flow across said first semi-conductor switch and said load resistor; and audio-means responsive to said oscillating means for generating an audio-signal.

2. The device of claim 1, wherein said supporting means has the form of a stick.

3. The device of claim 1, wherein said semi-conductor switch is a field effect transistor.

4. The device of claim 1, wherein said means for sensing comprises a first and second electrode, said first electrode surrounding said second electrode almost entirely and serving as said supporting means.

5. The device of claim 4, wherein said electrical siganl is a function of the resistance between said electrodes.

6. The device of claim 4, wherein said electrical signal is a function of the capacitance between said electrodes.

7. The device of claim 1, wherein said electrical device is powered by a battery.

8. The device of claim 7, wherein said battery comprises no more than three 1.5 volt, 100 microampere-hour cells.

9. The device of claim 7, wherein said battery comprises no more than two 1.5 volt, 100 microampere-hour cells.

10. The device of claim 1 further comprising:

dividing means for reducing said first frequency of said electrical pulses and for yielding electrical pulses at a second frequency; and said audio-means being activated by said electrical pulses at said second frequency.

11. The device of claim 10, wherein said oscillating means and said dividing means are built into an integrated chip.

12. The device of claim 10, wherein said calibrating means, said first semi-conductor switch, said oscillating means, said dividing means and said audio-means are housed in a cylindrical container surmounting said supporting means.

13. The device of claim 10, wherein said audio-means comprises:

a music synthesizer generating said audio-signal; and second means for amplifying said audio-signal.

14. The device of claim 13, wherein said music synthesizer is programmed to generate a popular melody.

* * * * *